United States Patent [19]

Kelly et al.

[11] 4,067,345
[45] Jan. 10, 1978

[54] METHOD AND COMPOSITIONS FOR RETARDING CHEMICAL DAMAGE TO HAIR WITH TREATING AGENTS CONTAINING TWO OR MORE POLAR GROUPS

[75] Inventors: Ralph Kelly, Cincinnati; Edmond Jean Ritter, Loveland, both of Ohio

[73] Assignee: Cincinnati Milacron Inc., Cincinnati, Ohio

[21] Appl. No.: 46,560

[22] Filed: June 15, 1970

Related U.S. Application Data

[63] Continuation-in-part of Ser. No. 696,509, Jan. 9, 1968, Pat. No. 3,630,934, which is a continuation-in-part of Ser. No. 613,095, Feb. 1, 1967, Pat. No. 3,538,009.

[51] Int. Cl.² .................... A45D 7/00; A45D 7/04; A61K 7/06; A61K 7/135
[52] U.S. Cl. .................................. 132/7; 8/10.2; 260/407; 424/DIG. 3; 424/62; 424/70
[58] Field of Search ................ 424/62, 70, DIG. 3; 8/10.2; 132/7; 260/407

[56] References Cited

U.S. PATENT DOCUMENTS

| | | | |
|---|---|---|---|
| 2,283,350 | 5/1942 | Baum | 424/62 |
| 2,606,199 | 8/1952 | Kienle et al. | 260/407 |
| 2,679,520 | 5/1954 | Groote | 260/407 X |
| 2,679,521 | 5/1954 | Groote | 260/407 X |
| 2,950,299 | 8/1960 | Kirkpatrick | 260/407 |
| 3,193,464 | 7/1965 | Edman et al. | 424/62 |
| 3,239,546 | 3/1966 | Rogier | 260/407 X |
| 3,251,869 | 5/1966 | Putnam et al. | 260/407 |
| 3,299,138 | 1/1967 | Sveum et al. | 260/407 X |
| 3,371,116 | 2/1968 | Nordgren et al. | 260/407 X |
| 3,536,810 | 10/1970 | Moculeski | 424/70 X |

*Primary Examiner*—Albert T. Meyers
*Assistant Examiner*—Vera C. Clarke
*Attorney, Agent, or Firm*—Plumley and Tyner

[57] ABSTRACT

The hair is protected from damage by chemical agents, e.g. in bleaching, by either pretreatment with, or concurrent use of a protective agent and the damaging chemical. The protective agents disclosed are organic compounds containing two or more polar groups, e.g. carboxyl groups, which are separated by at least 15 atoms the majority of which are carbon atoms and preferably containing a cyclic moiety of at least 5 atoms, e.g. the dimer of linoleic acid.

8 Claims, No Drawings

METHOD AND COMPOSITIONS FOR RETARDING CHEMICAL DAMAGE TO HAIR WITH TREATING AGENTS CONTAINING TWO OR MORE POLAR GROUPS

CROSS REFERENCES TO RELATED APPLICATIONS

This application is a continuation-in-part of Ser. No. 696,509, filed Jan. 9, 1968, now U.S. Pat. No. 3,630,934 which in turn is a continuation-in-part of Ser. No. 613,095, filed February 1, 1967, now U.S. Pat. No. 3,538,009.

BACKGROUND OF THE INVENTION

The fact that hair is damaged by a variety of chemical agents resulting in a reduction of both aesthetic and physical quality, is well-known. Most common is the damage caused by bleaching and dyeing operations. Also prevalent is damage resulting from too frequent shampooing or the use of harsh shampooing agents. Too, hair can be adversely affected during permanent waving. Damaged hair is recognized by one or more defects such as brittleness, split ends, scaling, low tensile strength, lack of luster, excessive elasticity, increased porosity, and poor manageability.

Hair damage is perhaps most pronounced as a result of bleaching and dyeing processes, particularly dyeing processes wherein oxidizing agents are used to develop the color of the dye. In bleaching, common agents include ammoniacal peroxide, alkali peroxide or mixtures of these with ammonium or potassium persulfate and the like. In oxidation dyeing, the most commonly practiced form of dyeing at the present time, the oxidizing agent is usually hydrogen peroxide. These are drastic treatments and the damage done to the hair during these treatments is well-recognized. It is also found that the almost inevitable contact of the surrounding skin areas with the bleaching or dyeing agents causes irritation manifested by redness of the skin and often by a burning sensation. While the commonly employed methods described suffer from these deficiencies, they are quite effective and therefore widely used. It is apparent that measures which would allow the continued use of the described procedures with a reduction in the problems associated therewith, would be a valuable contribution to the art.

It has now been found, in accordance with the present invention that damage to the hair resulting from chemical treatment such as with bleaching and dyeing agents can be prevented or retarded by treating the hair with a protective agent which is an organic compound containing two or more polar groups which are separated by at least 15 atoms the majority of which are carbon atoms and preferably containing a cyclic moiety of at least 5 atoms. The treatment of the hair with the protective agent can take place either prior to contact with the damaging agent or concurrently with treatment with the hair damaging agent.

Accordingly, it is an object of the present invention to provide a composition and a process for protecting the hair from degradation and adverse effects caused by treating agents.

It is also an object of the present invention to provide protection to the skin and scalp during hair treatment.

It is a more particular object of this invention to protect the hair during bleaching and oxidation dyeing processes.

Still another object of this invention is to reduce or eliminate the deficiencies exhibited by damaged hair such as split ends, scaling, reduced tensile strength, lack of luster, brittleness, excessive elasticity, and lack of manageability.

Still other objects of this invention will be apparent from the following description and claims.

As already noted, this invention involves the treating of hair either prior to the application of a damaging agent or concurrently with the application of a damaging agent with a protective agent which is an organic compound containing two or more polar groups separated by at least 15 atoms the majority of which are carbon atoms and preferably containing a cyclic moiety of at least 5 atoms. The protective agents are simply applied from aqueous compositions. The concentration of the protective agent can vary widely although a concentration of about 0.1 to 20% by weight of the composition is generally useful. A preferred range for most purposes is about 0.5 to 10% by weight of the composition. As will be seen from the following discussion; compatibility of the protective agents and various compositions should present little problem since a wide variety of protective agents are disclosed including anionic, cationic and non-ionic materials.

As used herein, the term "polar group" is meant to define a group having a dipole moment and containing at least one nitrogen, oxygen, phosphorus, sulfur or combinations thereof. These groups are deemed to be capable of hydrogen bonding with the protein, although the formation of stronger bonds such as covalent bonds is not excluded. The cyclic moiety is preferably a carbocyclic, i.e. cyclic hydrocarbon moiety of 5 to 18 carbon atoms which can be saturated or can contain from 1 to 9 double bonds and can contain one or more substituents on the ring. Heterocyclicmoieties which contain the structures —O—, —S—, —N—, or —NH— in the ring can also be present in the protective agent and serve as the necessary cyclic moiety.

In accordance with the present invention, it has been discovered that hair damage caused by the contact of chemicals, particularly oxidizing agents can be reduced or eliminated by contacting the hair with the compounds of the general type above either prior to contact with the damaging agent or concurrently with the damaging agent. Rinsing of the hair with water or a mild soap solution after application of the protective agent but prior to the application of the irritant does not cause a significant change in the effect of the protective agent when a damaging agent is subsequently applied. This and other types of evidence, such as electrophoretic studies of mixtures of soluble proteins and protective agents, have shown that some form of interaction occurs between keratin and the protective agent. Although the complex formed between protein molecules and the protective agent can be isolated by the indicated electrophoresis, the specific nature of the complex has not yet been established. It is presumed, however, that both adsorption and some form of chemical interaction are involved. It is further theorized that the cyclic structure which is preferred in the protective agent aids in the adsorption of the agent onto the keratin of the hair and that the polar groups of the protective agent interact with the protein molecules of the keratin.

In addition to the requirement that the protective agent contain at least two polar groups, the polar groups of the protective agent must also be separated by a chain of at least 15 atoms, a majority of which should be carbon atoms. However, the presence of additional polar groups located intermediary to the described two terminal polar groups does not appear to interfere in the protective effect. It is believed that as a result of this chain length, the indicated polar groups are capable of and do interact with different protein molecules. The damaging action of chemicals such as oxidants is believed to be caused by a degradation of the protein molecules. This damage is irreparable and results in brittleness, scaliness, split ends, loss of luster and the like. The protective agents employed in the compositions of the present invention are believed to counteract this breakdown by providing additional bridges between the protein molecules of the keratin layer, which maintain the integrity of the keratin. It is to be understood, however, that we do not wish to be bound by the foregoing explanation of the activity of the protective agents of the present invention, and that such explanation is only set forth for a better understanding of the present invention.

The protective agents of the present invention contain at least two polar groups separated by an organic radical of at least 15 atoms, a majority of which are carbon and which preferably contains a cyclic group. The polar groups should be compatible with the total composition and should be of the type capable of existing in the aqueous phase, i.e. without irreversibly reacting with the water. Additional polar groups may be present in this divalent radical or may be located on branches attached to this radical. Such additional polar groups do not interfere in the effectiveness of the protective agent. The two polar groups described can be the same or different. Suitable polar groups include hydroxyl (—OH); carboxyl (—COOH); ester (R'O—CO—, wherein R' can be aliphatic, cycloaliphatic, or aromatic radical of 1–12 carbon atoms, or can be part of a polyester chain); amino (—NH$_2$); substituted amino (NHR'' or —NR''R''', wherein R'' or R''' are aliphatic or aromatic hydrocarbon radicals of 1–12 carbon atoms, or wherein R'' and R''' can combine to form 3- to 6-membered rings with the nitrogen, or wherein R'' is part of a polyamine chain); amido

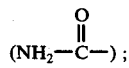

substituted amido

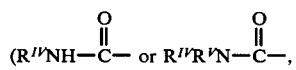

wherein R$^{IV}$ and R$^V$ are aliphatic or aromatic hydrocarbon radicals of 1–12 carbon atoms and R$^{IV}$ can be part of a polyamide chain); quaternary ammonium salts

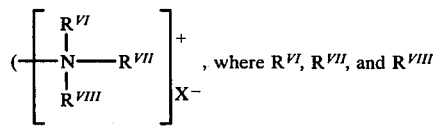

where R$^{VI}$, R$^{VII}$, and R$^{VIII}$ are lower alkyl radicals and X is an anion such as a halogen ion); sulfate (—SO$_4$Me, where Me is a metal and preferably an alkali metal); sulfonate (—SO$_3$Me); sulfonamide (—SO$_2$NH$_2$); substituted sulfonamide (—SO$_2$NHR$^{IV}$ or —SO$_2$NR$^{IV}$R$^V$); thio acid salts (—COSMe); thioesters

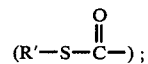

sulfoxides (=SO); sulfonic acid (—SO$_3$H); sulfinic acid (—SO$_2$H); phosphate (—HMePO$_4$ or —Me$_2$PO$_4$); and phosphonium salts (—HPO$_3$Me). The preferred polar groups employed in the protective agents of the present invention are those which contain, aside from any metal or halogen which may be associated with the polar group in ionic form, carbon and oxygen or carbon and nitrogen. In general, functional groups of greater polarity are preferred over those of lesser polarity. It will be apparent that the size of any of the described substituents and particularly hydrocarbon substituents on the polar groups will affect the polarity. In general, the preferred substituents on the polar groups are lower alkyl groups and such water-solubilizing groups as polyoxyalkylene radicals, in particular polyethylene glycol chains.

The effectiveness of the protective agent in preventing skin irritation not only requires the presence of at least two polar groups in the protective agent, but also the separation of the polar groups by an atom chain of at least 15 atoms, the majority of which are carbon atoms. The presence of additional polar groups does not interfere in the function of the two polar groups separated by the necessary number of atoms, regardless of whether these polar groups are part of such chain or located on side branches of the molecule. The presence of more than two polar groups each of which are separated by 15 or more atoms increases the effectiveness of a protective agent in which the polar groups are weak polar groups, such as hydroxyl groups, but does not appear to add significantly to the effectiveness of a protective agent containing at least two strong polar groups such as carboxyl groups separated by the necessary linking chain.

Although the minimum size of the linking radical is determined by the length of the chain separating the polar groups, the maximum size of the linking radical is determined by the dispersibility of the protective agent in the medium in which it is incorporated. Thus compounds which are not liquid or colloidally dispersible are not suitable in the present invention. Hence, the upper limit of the size of the linking radical is determined not only by the number of atoms in the linking radical, but also by the presence of additional polar groups in the linking radical which can increase the dispersibility of the protective agent, as well as the nature of any radical attached to the polar group. In general, however, the linking radical contains less than 80 atoms. As indicated, the linking radical has, preferably, a carbon backbone structure which can be aliphatic, cycloaliphatic, or aromatic in nature. The required carbocyclic or heterocyclic moiety need not be part of the backbone structure. Particularly effective are hydrocarbon linking radicals which contain a cycloaliphatic or aromatic ring structure. In addition to the preferred hydrocarbon structure, the linking radical can also be in the form of a polymeric structure such as a polyester, polyether, polyamide, or polyamine. Although other polymeric linking radicals will be apparent to those skilled in the art, many of these radicals are excluded by virtue of the limitations with respect to solubility or colloidal dispersibility required to give rise to the protective properties. The preferred polymeric linking radicals are the polyether radicals derivable from polyoxyalkylene ethers, containing 2 to 30 oxyalkylene units in which the alkylene radical contains from 2 to 4 carbon atoms. The polyoxyalkylene units can, in addition, contain ester groups. Thus, suitable linking radicals are obtained by the reaction of a polyoxyalkylene glycol with a polycarboxylic acid.

It is apparent that the protective agent can be present in the compositions in the form of a suitable salt. For instance, protective agents such as dimer acid can be used as the sodium, potassium, ammonium or triethanolamine salt. Other salts appropriate to the particular composition can be used. Similarly, amine group containing protective agents can be used in the salt form. The selection of the appropriate salt is within the skill of the art and will depend on the nature of the other ingredients, solubility and similar considerations.

The following classes of materials are protective agents suitable for use in the present invention.

A. The polymerized product of 2 to 4 molecules of a monomeric $C_{12}$ to $C_{26}$ fatty acid, said product containing 2 to 4 carboxyl groups; or in place thereof derivative radicals selected from the group consisting of carboxyl salt; hydroxyl; unsubstituted amino; substituted amino wherein the substituents are aliphatic or aromatic hydrocarbon radicals of 1 to 12 carbon atoms, or said substituents taken together form a 3 to 6 membered carbocyclic or heterocyclic ring with the amino nitrogen; unsubstituted amido; substituted amido wherein the substituents are aliphatic or aromatic hydrocarbon radicals of 1 to 12 carbon atoms, or said substituents taken together form a 3 to 6 membered carbocyclic or heterocyclic ring with the amido nitrogen; quaternary ammonium wherein the nitrogen substituents are alkyl of 1 to 6 carbon atoms; lower alkyl ester; sulfate; sulfonate; phosphate; phosphonate; and derivative compounds containing further substituents in said alkyl, aliphatic or aromatic hydrocarbon radicals selected from the group consisting of carboxyl and the said derivative radicals.

Among the cationic protective agents defined in A which can be utilized in this invention are fat polyquaternary ammonium compounds having the formula:

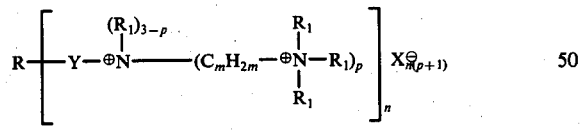

in which R is the hydrocarbon radical of the polymeric fat acids, R(COOH)$_n$ obtained by polymerization of an unsaturated higher fatty acid containing 12 to 26 carbon atoms;

$R_1$ is an aliphatic hydrocarbon group having from 1 to 6 carbon atoms;
X is an anion;
Y is an alkylene radical having 1 to 8 carbon atoms;
m is 3 or 4;
n is 2 or 3; and
p is 0, 1, or 2.

The polymeric fat acids from which the quaternary ammonium compounds employed as protective agents in the present invention are derived are polymerization products of unsaturated fatty acids containing from 12 to 26 carbon atoms and generally have a degree of polymerization of two to four. Quaternary ammonium compounds prepared from fatty acid mixtures containing such dimer, trimer, or tetramer acids are also useful. Quaternary ammonium compounds of the type useful in the present invention are disclosed in U.S. Pat. Nos. 3,073,864 and 3,299,138, the disclosure of which patents is incorporated herein by reference.

B. Esters and polyesters of cycloaliphatic or aromatic polycarboxylic acids containing at least one 5 to 7 carbon ring and polyoxyalkylene ethers containing 2 to 30 oxyalkylene units in which the alkylene radical contains 2 to 4 carbon atoms. The benzene, naphthalene, cyclohexane, cyclopentane, cycloheptane, and diphenyl polycarboxylic acids are suitable. Among the preferred polycarboxylic acids are the benzene, di-, tri-, and tetra-carboxylic acids, the corresponding dihydrobenzene (cyclohexadiene), tetrahydrobenzene (cyclohexene), and cyclohexane polycarboxylic acids. The degree of polymerization can vary widely so long as the requirements that the compounds contain at least 15 atoms between the polar groups and the proper solubility or dispersibility characteristic in aqueous media are maintained. The polyoxyalkylene ether can contain further substituents such as shown in Compounds 47 and 51 in Example 1.

C. Esters and polyesters of the polymerized fatty acid defined in A above and a polyol selected from the group consisting of
a. polyoxyalkylene ethers containing 2 to 30 oxyalkylene units in which the alkylene radical contains 2 to 4 carbon atoms;
b. condensation products of ethylene oxide with a hydrophobic base formed by the condensation of propylene oxide with propylene glycol, having the general formula:

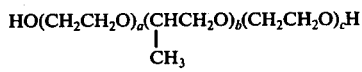

wherein
a is 1 to 150
b is 15 to 70 and
c is 1 to 150;

c. condensation products of alkylene oxides having 2 to 4 carbon atoms and polyamines having 2 to 4 amino groups and containing 2 to 8 carbon atoms in an aliphatic, cycloaliphatic or aromatic group. The alkylene oxide addition units can comprise block or random copolymer units as well as homopolymer units. Specific materials of this type having the following formula have been found to be particularly useful in this invention:

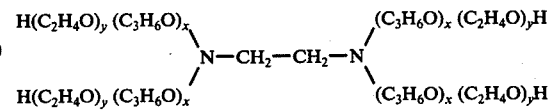

where x is 2 to 10 and y is 2 to 15.

The protective agents described in A, B and C, i.e. those which must contain a cyclic moiety are preferred over those broadly disclosed which do not necessarily contain a cyclic moiety.

As previously indicated, the protective agents are used primarily for the purpose of shielding the hair from the adverse effects of harsh chemicals. No particular effect is seen in restoring hair already damaged. The protective agents do, however, favorably effect the manageability and luster of hair either healthy or damaged. Accordingly, to obtain these benefits as well as to reduce skin irritation, the protective agents are recommended for use in shampoos, hair rinses and the like, particularly where the hair will subsequently be subjected to contact with damaging chemicals such as bleaches and dyes.

The cationic protective agents, especially the class of quaternized polymerized fatty acid amines, mentioned above, are favored in hair rinses. These quaternary compounds can also be advantageously incorporated into a combination shampoo-rinse product if a non-ionic or amphoteric surfactant is used.

It should be mentioned that the presence of protective agent is found to have little or no effect on the basic functions of the compositions in which they are incorporated whether these compositions be bleaches, dyeing compositions, tints, permanent wave solutions, shampoos, grooming preparations or the like.

The following examples are intended to illustrate the nature of the invention more fully but are not to be taken as a limitation on the scope thereof.

EXAMPLE 1

This example illustrates several of the methods which are used to determine whether a given chemical substance possesses activity as a protective agent for keratin, and lists representative materials which have been determined to have such activity based on one or more of the described tests.

Several of the listed protective agents have been tested by each of the methods described below and a number of protective agents have been subjected to at least two of the tests. Good correlation of results have been found between the various tests.

A. ANIMAL IMMERSION TEST

A female, albino guinea pig, weighing about 300 to 325 g, is immersed up to the thoracic region in the test solution at 40° C for 4.5 hours per day on three successive days. Each animal is thoroughly rinsed and dried after each immersion. Three days after the last immersions, the skin of each animal is examined for gross changes, and grades are assigned which represent the degree of damage to the skin. In general, three animals are tested simultaneously in the same solution. The grading system is based on a scale of 1 to 10, in which the numbers have the following meanings.

| Grade or Rating | Gross Reaction | Skin Damage |
|---|---|---|
| 1 | Severe cracking and bleeding; death of animal in most instances | Extremely severe; death of skin tissue |
| 2 | Severe cracking; moderate bleeding | " |
| 3 | Severe cracking; slight to moderate bleeding | Severe |
| 4 | Moderate cracking | " |
| 5 | Slight cracking | Moderate |
| 6 | Severe scaling | " |
| 7 | Edema; slight to moderate scaling | " |
| 8 | Slight scaling and moderate edema | Slight |
| 9 | Slight redness and edema | " |
| 10 | Normal | Normal |

Despite the fact that this exposure test is conducted using extremely dilute solutions, it is an exaggerated test, as compared to human exposure; although it has been established (see Canadian Pat. No. 639,398) that the test correlates extremely well with the skin irritation effect observed on human skin.

In preparing the test solution, a 100 g concentrate is first prepared which is then employed in the test solution in 1% by volume concentrations. In order to prepare a homogeneous concentrate which is readily dilutable, the following additional ingredients were added as indicated: Igepal CA-630, a commercially available nonionic wetting agent of octylphenoxypoly(oxyethylene)ethanol; triethanol amine, and capric acid. The triethanol amine (TEA) is employed to allow salt formation of mildness additives employed in combination with anionic detergents and the capric acid (Cap. A.) is employed for the same purpose in combination with cationic detergents. In general, the irritant and the protective agent are each employed in the examples illustrated below in a concentration of 15 weight percent based on the described 100 g concentrate.

A difference of about 2 units between the control animal (immersed in irritant) and the test animal (immersed in irritant containing protective agent) under the given conditions is generally considered to indicate a satisfactory protective effect.

A typical irritant used in the above-described test is sodium lauryl sulfate, but a variety of irritant materials have been used, including alkali, such as sodium and ammonium hydroxide, and oxidants such as hydrogen peroxide. In general, a material which exhibits protective properties with a given irritant is found to exhibit similar properties with other irritants.

Further details of the above-described test are found in Ser. No. 696,509 filed Jan. 9, 1968 and Ser. No. 613,095 filed Feb. 1, 1967, the disclosure of which is incorporated herein by reference.

B. OCCLUSIVE PATCH TEST (a modified version of the Finkelstein patch test)

Female albino guinea pigs, weighing between 280 and 320 grams are shaved, and one application of 7.4% formalin applied. A quantity of 0.15 milliliters of each protective agent is applied to part of the test area and rubbed into the skin approximately 10 times in each direction. After a drying time of one-half hour, a solution of the irritant is applied to a test pad which is placed over the test site and secured by tape. The pad and tape is then covered by a plastic sheet which is secured at the extremes of the abdominal area. 2.0 cc of trypan blue dye PPS was injected into each axila of the test animal. After 18 hours, the pads were removed and the test sites examined for degree of intensity of the dye which had accumulated at the test site. Dye accumulation was evaluated on the scale of 0 to 100, 0 being the intensity of dye when no protective agent was applied, and 100 being no visible dye accumulation. Variations of dye intensity of about 5% or more between test and control is considered significant. The following scale is also used to interpret results:

| Rating Scale | (% Protectability) |
|---|---|
| 80–100 | Excellent |
| 70–80 | Good |
| 60–70 | Minimal |
| 50–60 | Irritating |
| 0–50 | Very irritating |

C. ELECTROPHORESIS

The prescribed procedure for paper electrophoresis is followed. This involves placing a sample on a paper strip, mounting the strips in a closed cell filled with a buffer (pH 8.6 most often used), and connecting the apparatus to a power supply. Thus, degree of mobility of the sample along the strip in a given time can be measured. When applied to keratin, protective agents and skin irritants or agents which degrade keratin samples, the degree of mobility indicates that an interaction takes place between protein and the protective agent, since this combination exhibits a mobility less than keratin along. The combination of keratin and skin irritant or keratin and an agent which degrades protein, on the other hand, exhibits a mobility greater than protein. The differences in degree of mobility are indicative of the efficacy of the protective agent.

D. MICROSCOPIC STUDIES

Keratin, particularly hair, is subjected to a degradating agent with and without pretreatment with, or incorporation of, a potential protective agent. Protective qualities are evidenced by reduced physical deterioration, especially scaling.

E. TENSILE MEASUREMENTS ON HAIR

Clean human hair is subjected to the action of normally degradating hair treating chemicals with or without the incorporation of a potential protective agent.

The tensile strength properties of the hair are determined and taken as a measure of the degradation of the hair produced by the treatment. Various methods to measure the tensile properties of human hair are known; one such method being that of Beyak, Meyer and Kass, published in J. Soc. Cosmetic Chemists, 20, 615–626 (1969). A modification of that method is used. The hair is tested at 25° C and ambient room humidity. The loading rate is 2.0 inches per minute. A Stratham Universal transducing cell is affixed between the movable upper head of the tester and the upper jaws of the sample holder. The output of the transducer load cell is led to a Sanborn 150 recording unit so that a stress/strain curve and elongation of each individual hair fiber can be recorded during its loading to failure.

The following materials have been found to possess protective qualities for keratin by one or more of the methods described above. Suitable protective agents which are based on a fatty acid dimer linking radical include the following in which [D] represents the carboxyl-free residual of a dimerized fatty acid and [T] represents the carboxylfree residue of a trimer acid.

Specific materials disclosed in Ser. No. 696,509, filed Jan. 9, 1968, (incorporated by reference above) now U.S. Pat. No. 3,630,934, are particularly materials comprising the dimer of linoleic acid, commercially available as EMPOL 1022, and derivatives of this dimer acid. EMPOL 1022 in its crude form contains in addition to dimerized linoleic acid 2–5% of unpolymerized linoleic acid and 19–22% of trimer acid. The specific materials shown in Ser. No. 696,509 include dimerized linoleic acid in its crude commercial form as indicated above, dimer ester, dimer amide, dimer morpholide, and dimer amine.

The dimer ester was prepared from the dimer acid by esterification with a polyethylene glycol having a molecular weight of 400 in a molar ratio of acid-to-polyether of 1:1.25 until an acid number of five was obtained. The dimer amide employed is the reaction product of one mole of dimer acid with four moles of diethanol amine. The dimer morpholide employed is the reaction product of four moles of morpholine with one mole of dimer acid. The dimer amine employed is a commercially available compound in which the carboxyl groups of the dimer acid are replaced by amino methyl ($-CH_2NH_2$) groups.

The following materials have been found to possess protective qualities for keratin by one or more of the methods described above 1. 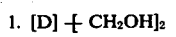 $[D] + CH_2OH]_2$ 2. 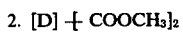 $[D] + COOCH_3]_2$ 3. 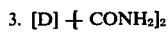 $[D] + CONH_2]_2$ 4. 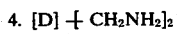 $[D] + CH_2NH_2]_2$ 5. 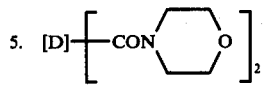

6. 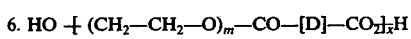 $HO + (CH_2-CH_2-O)_m-CO-[D]-CO_2]_xH$ $m = 2$ to $30$; $x = 1$ to $10$ 7.  $[D] + CH_2-SO_4Na]_2$ 8. 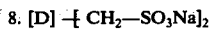 $[D] + CH_2-SO_3Na]_2$ 9. 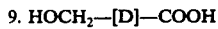 $HOCH_2-[D]-COOH$ 10. 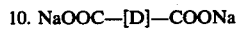 $NaOOC-[D]-COONa$ 11. 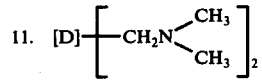

12. 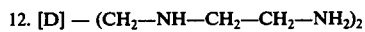 $[D] - (CH_2-NH-CH_2-CH_2-NH_2)_2$

13.  $[D] - (CH_2-NH-CH_2-CH_2-CH_3)_2$

14.  $[D] + CH_2PO(C_4H_9)_3 \,^+Br^-]_2$

15. 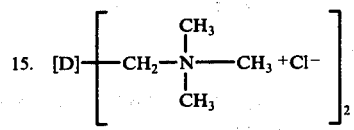

16. 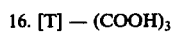 $[T] - (COOH)_3$

17. 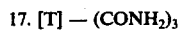 $[T] - (CONH_2)_3$

18. 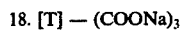 $[T] - (COONa)_3$

19. 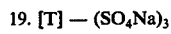 $[T] - (SO_4Na)_3$

20. 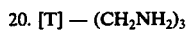 $[T] - (CH_2NH_2)_3$

21.  $[D] + COO^-(NH[CH_2CH_2OH]_3)\,^+]_2$

22. Reaction product of dimer acid and hydroxyethyl ethylene diamine. The product is shown as a diester but consists of a mixture of ester, half ester-half amide, diamide and oxazoline.

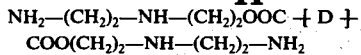

23. Diester of dimer acid and a polyoxyalkyleneated ethylenediamine

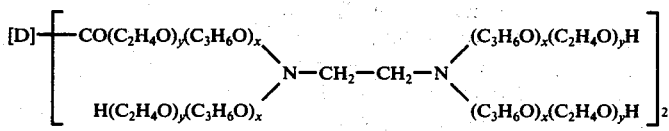

where x is from about 2 to about 10 and y is from about 2 to about 15

24. Reaction product of dimer acid and N-amino-propyl diethanolamine. The product is shown at the diamide, but contains also the ester and ester-amide.

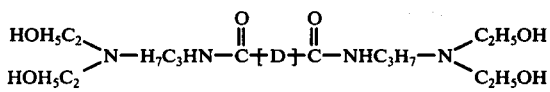

25. Dimer diethanolamide. This product also contains sizable quantities of the oxazoline.

[D] ⫤ CONHC₂H₅OH]₂

26. Bis(hydroxyethyl)dimerate

[D] ⫤ COOCH₂CH₂OH]₂

27. Dimer acid or soap thereof

[D]— [COOX]₂ wherein X is H, Na, K, or

—C₂H₅N(C₂H₅OH)₂

28. Dimer diamine diacetate

[D] — [N(COOCH₃)₂]₂

29. The reaction product of dimer acid and N-cyclohexyl-1,3-propane diamine

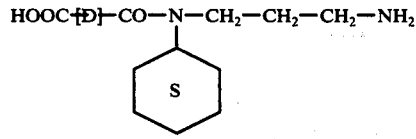

30. Polyethylene glycol ester of dimer acid

[D] ⫤ COO(C₂H₄O)ₓH]₂

31. Carbitol diester of dimer acid

[D]— [COO(C₂H₄O)₂C₂H₅]₂

32. Dipropylene glycol ester of dimer acid

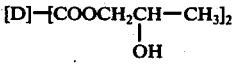

33. Dimer sulfate

[D] ⫤ CH₂SO₄H]₂

34. Polymeric ester of N-N-di(2-hydroxyethyl)aniline and dimer acid

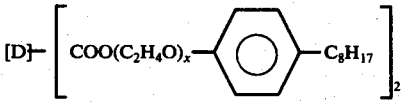

35. Octylphenoxypolyethoxyethanol diester of dimer acid

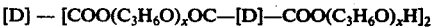

x = 4 to 10

36. Polyester of polypropylene glycol and dimer acid

[D] — [COO(C₃H₆O)ₓOC—[D]—COO(C₃H₆O)ₓH]₂ x = about 6 to about 25

37. Ester of polybutylene glycol and dimer acid

[D] — [CO(OC₄H₉)ₓH]₂ x = 10 to 20

38. Dimer glycol acetate

[D] ⫤ CH₂OO—C—CH₃]₂

39. N,N'-bis-3-aminopropyl dimer diamine

[D] — [NC₃H₇NH₂]₂

40. Oleyloxypolyethoxyethanol ester of dimer acid

[D] — [CO (OC₂H₄)ₙ
—O—(CH₂)₈—CH=CH(CH₂)₇—CH₃]₂ n = about 10

41. Monostearyl-monopolyethylene glycol ester of dimer acid

C₁₇H₃₅OCO— D] 73 CO [OC₂H₄]ₓOH $X$ = about 9

42. Dimer tetramine

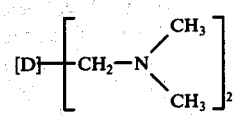

[D]—CH$_2$—NH CH$_2$CH$_2$CH$_2$NH$_2$]$_2$

43. Tetramethyl dimer diamine

44. Mixed ester of reaction of pyromellitic anhydride with octylphenoxypolyethoxyethanol and subsequent reaction with the polyol resulting from reaction of ethylene and propylene oxides with ethylene diamine.

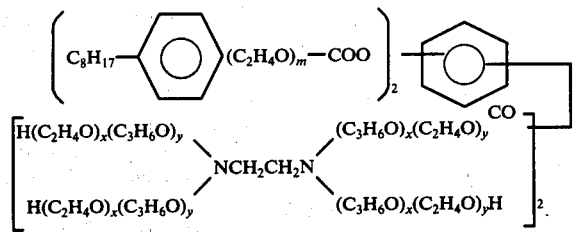

x = about 7, y = about 9, m = 4 to 10

45. Tetrakis-(3-carb-octylphenoxypolyethoxybenzoyl) ester of the tetrol resulting from ethylene oxide and propylene oxide addition to ethylene diamine.

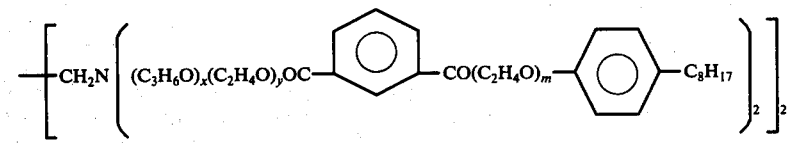

x = about 7 y = about 9 m = 4 to 10

46. Terephthalic acid ester of polyethylene glycol

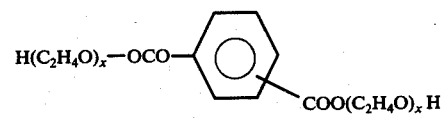

x is 4 25

47. Tetrahydrophthalic acid ester of polyethylene glycol

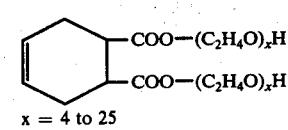

x = 4 to 25

48. p-Pyromellitic acid ester of polypropylene glycol

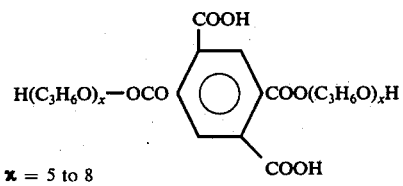

x = 5 to 8

49. Tris(octylphenoxypolyethoxyethyl) trimesate

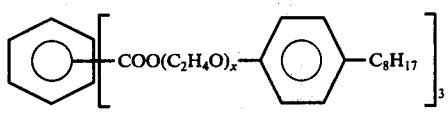

EXAMPLE 2

This example illustrates the use of the protective agents of this invention in hair bleaches and hair dyes.

The following compositions were prepared and applied to normal hair for 4–20 hours at 25° C.

| Hair Bleaches | Parts by Weight | |
|---|---|---|
| Hydrogen Peroxide (6%) | 70 | 70 |
| Ammonium Hydroxide (28%) | 10 | 10 |
| Oleic Acid | 20 | — |
| Dimer Acid | — | 20 |
| Hair Dyes | Parts by Weight | |
| Oleic diethanolamide | 15.0 | 15.0 |
| O-phenylenediamine | 2.0 | 2.0 |
| Ammonium Hydroxide (28%) | 10.0 | 10.0 |
| Sodium Sulfite | 0.2 | 0.2 |
| Propylene Glycol | 10.0 | 10.0 |
| Oleic Acid | 20.0 | — |
| Isopropyl alcohol | 10.0 | 10.0 |
| Distilled water | 32.8 | 32.8 |
| Hydrogen Peroxide (6%) | 100.00 | 100.00 |
| Dimer Acid | — | 20.0 |

The treated hair was examined microscopically. In both instances where dimer acid protective agent was substituted for oleic acid the hair exhibited less scaling indicating less damage due to the oxidizing agents present.

EXAMPLE 3

This example illustrates the effect of pretreatment of hair with protective agent prior to treatment with oxidizing agent.

Hair pretreated with an aqueous ammonium hydroxide solution containing 20% by weight of dimer acid and oleic acid, respectively, was subsequently treated with the oleic acid containing bleach and dye compositions of Example 2. Protective effects similar to those found in Example 2 were noted for the hair pretreated with the dimer acid composition.

EXAMPLE 4

This example illustrates the effect of the protective agents of this invention upon the tensile strength of hair.

Hair was pretreated with a bleaching type solution containing (a) 70 parts of 6% (20 vol) hydrogen peroxide and 10 parts of 10% ammonium hydroxide, and (b) 20 g of either (1) oleic acid, (2) dimer acid or (3) the mixed ester resulting from the reaction of pyromellitic dianhydride first with octyl phenoxy tetraethoxy ethanol and then with a polyol which is the product of reaction of ethylene diamine with propylene oxide and ethylene oxide in a block process corresponding to compound No. 44 in Example 1. The hair swatches were immersed in the three above solutions for 8.0 hours at 25° C, then removed and rinsed in tap water. The hair was dried and 10 to 25 strands were selected from each hair swatch for testing of tensile properties.

The tensile properties of the original hair sample with no treatment and the three treated hair samples were determined as described in Example 1. The results are tabulated in Table I.

TABLE I

| Treatment | Yield Strength (grams) | Break Strength (grams) | Relative Percent Elongation |
|---|---|---|---|
| None | 66.8 | 105.7 | 100 |
| Oleic Acid | 55.4 | 92.5 | 122 |
| Dimer Acid | 55.9 | 102.4 | 106 |
| No. 44 of Example 1 | 58.0 | 115.7 | 111 |

The agents of this application retain the elastic properties of normal untreated hair significantly better than does the oleic acid. All the hair samples begin to plastically deform at a lower level of stress after exposure to the harsh ammoniacal peroxide solutions. The oleic acid control representing compositions of the type currently in use shows greater elongation and a lower ultimate strength. The agents of this application prevent much of the peroxide damage as evidenced by retention of normal hair elongation and breaking strength.

In another test of this type, but employing as the harsh hair treating solution a mixture of 15 parts ammonium persulfate and 40 parts 6% (20 vol) hydrogen peroxide containing in one case 9% of triethanolamine salt of dimer acid as the protective agent and in the other 9% of triethanolamine salt of oleic acid as the control, it was found that hair treated with the solution containing the protective agent had a breaking strength of 106.8 grams while the control hair was severely degraded and had a breaking strength of only 65.4 grams.

EXAMPLE 5

Hair treating experiments were carried out by professional hair stylists on a large group of human subjects. These tests were carried out on a so-called "half-head" basis in which a standard hair bleaching and/or hair dyeing solution was applied to one side of the head of a subject and the same standard hair bleaching and/or hair dyeing solution modified by inclusion of 9% of a protective composition of this application was applied to the other side of the head. The effects of the protective agent were visually evaluated by the hair stylists. The protective agents improved the hair luster and manageability. They also improved the ease of application of the hair treating solutions. Microscopic examination of the hair from the side of the head which has been treated with the solution containing the protective agent showed that there were fewer split ends, and a lower incidence of scaling damage. Additionally, almost all the test subjects noticed a freedom from stinging, burning, irritation of the scalp, forehead, and nape of the neck on the side of the head treated with the irritating solutions containing the protective agent.

In a second series of tests the protective agents were applied at the 2% level in water to human subjects on a half-head basis as a grooming aid. The hair luster and manageability were improved by the protective agents.

EXAMPLE 6

This example illustrates a typical hair rinse composition containing the protective agent of this invention. Protective agents, particularly those of the cationic type, have been incorporated into a variety of known hair rinse formulations.

The following composition was representative of those prepared:

| | Parts by Weight |
|---|---|
| Dimer diamine quaternized with methyl chloride | 5 |
| Water | 83 |
| Glycerol monostearate | 4 |
| Amerchol L 101 (lanolin sterols and alcohols | 5 |
| Ethoxylated lanolin | 2 |
| Hexadecanol | 1 |

This composition improved the wet combing and manageability characteristics of hair and exhibited a 100% protectability as measured by the patch test (see Example 1). The corresponding composition wherein Hyamine 2389 was substituted in equal amounts for the quaternized dimer diamine also imparted good wet combing and manageability characteristics but only imparted 55% protectability in the patch test.

What is claimed is:

1. In a process for treating hair comprising subjecting hair to an aqueous hair damaging composition, the improvement comprising reducing the degree of hair damage by applying to the hair prior to or concurrently with subjecting the hair to said hair damaging composition, an aqueous composition containing protective agent in an amount effective to reduce the degree of hair damage, said protective agent being compatible and dispersible in the aqueous composition by which it is applied to the hair; said protective agent being an organic compound containing at least two polar groups separated by a chain of at least 15 atoms, a majority of which are carbon atoms, and which contains a cyclic moiety; said polar groups selected from the class consisting of carboxyl; carboxyl salt in which the salt forming group is a metal, ammonia or an amine; hydroxyl; amino; substituted amino wherein the substituents are aliphatic or aromatic hydrocarbon radicals of 1 to 12 carbon atoms, or said substituents taken together form a 3 to 6 membered carbocyclic or heterocyclic ring with the amino nitrogen; amido, substituted amido wherein the substituents are aliphatic or aromatic hydrocarbon radicals of 1 to 12 carbon atoms, or said substituents taken together form a 3 to 6 membered carbocyclic or heterocyclic ring with the amido nitrogen, quaternary ammonium wherein the nitrogen substituents are alkyl of 1 to 6 carbon atoms; lower alkyl ester; sulfate; sulfonate; phosphate; phosphonate; and polar groups containing further substituents in said alkyl, aliphatic or aromatic hydrocarbon radicals selected from the class defined above.

2. Process of claim 1 in which said protective agent is selected from the group consisting of esters and polyesters of cycloaliphatic or aromatic polycarboxylic acids containing at least one 5 to 7 carbon ring and a hydroxy compound comprising a polyoxyalkylene ether containing 2 to 30 oxyalkylene units in which the alkylene radical contains 2 to 4 carbon atoms.

3. The process of claim 1 in which said hair damaging composition is a hair bleaching composition.

4. The process of claim 1 in which said carboxyl salt polar group is a sodium, potassium, ammonium, or triethanolamine salt.

5. The process of claim 1 in which hair is treated with a hair damaging bleaching composition subsequent to the step of subjecting the hair to said aqueous composition containing protective agent.

6. An improved aqueous hair bleaching composition consisting essentially of a hair damaging hair bleaching composition and protective agent compatible and dispersible therein, in an amount effective to reduce the amount of damage to the hair; said improved hair bleach composition causing reduced hair damage when used for bleaching hair compared to the composition without the protective agent; said protective agent being an organic compound containing at least two polar groups separated by a chain of at least 15 atoms, a majority of which are carbon atoms, and which contains a cyclic moiety; said polar groups selected from the class consisting of carboxyl; carboxyl salt; hydroxyl; amino; substituted amino wherein the substituents are aliphatic or aromatic hydrocarbon radicals of 1 to 12 carbon atoms, or said substituents taken together from a 3 to 6 membered carbocyclic or heterocyclic ring with the amino nitrogen; amido; substituted amido wherein the substituents are aliphatic or aromatic hydrocarbon radicals of 1 to 12 carbon atoms, or said substituents taken together form a 3 to 6 membered carbocyclic or heterocyclic ring with the amido nitrogen; quaternary ammonium wherein the nitrogen substituents are alkyl of 1 to 6 carbon atoms; lower alkyl ester; sulfate; sulfonate; phosphate; phosphonate; and polar groups containing further substituents in said alkyl, aliphatic or aromatic hydrocarbon radicals selected from the class of polar groups defined above.

7. The composition of claim 6 in which the carboxyl salt polar group is a salt of sodium, potassium, ammonium or triethanolamine.

8. Composition of claim 6 in which said protective agent is selected from the group consisting of esters and polyesters of cycloaliphatic or aromatic polycarboxylic acids containing at least one 5 to 7 carbon ring and a hydroxy compound comprising a polyoxyalkylene ether containing 2 to 30 oxyalkylene units in which the alkylene radical contains 2 to 4 carbon atoms.

* * * * *